US007638618B2

(12) United States Patent
Habermann

(10) Patent No.: US 7,638,618 B2
(45) Date of Patent: Dec. 29, 2009

(54) NUCLEIC ACIDS ENCODING A HIRUDIN AND PRO-INSULIN AS SUPERSCRETABLE PEPTIDES AND FOR PARALLEL IMPROVEMENT OF THE EXPORTED FORMS OF ONE OR MORE POLYPEPTIDES OF INTEREST

(75) Inventor: Paul Habermann, Eppstein (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 331 days.

(21) Appl. No.: 10/076,631

(22) Filed: Feb. 19, 2002

(65) Prior Publication Data

US 2003/0028001 A1 Feb. 6, 2003

Related U.S. Application Data

(60) Provisional application No. 60/270,592, filed on Feb. 23, 2001.

(30) Foreign Application Priority Data

Feb. 20, 2001 (DE) .................................. 101 08 100

(51) Int. Cl.
C07H 21/04 (2006.01)
C12P 21/02 (2006.01)
C12N 15/12 (2006.01)
C12N 15/17 (2006.01)

(52) U.S. Cl. .................. 536/23.4; 536/23.51; 435/69.7; 435/69.4

(58) Field of Classification Search ................ 530/350; 536/23.1, 23.4, 23.51; 514/12; 435/69.1, 435/69.7, 69.4

See application file for complete search history.

(56) References Cited

U.S. PATENT DOCUMENTS

| 5,095,092 A | 3/1992 | Badziong et al. |
| 5,316,947 A | 5/1994 | Crause et al. |
| 5,434,073 A * | 7/1995 | Dawson et al. ............... 435/216 |
| 5,677,172 A | 10/1997 | Makarow |
| 5,705,355 A | 1/1998 | Tolstoshev et al. |
| 5,824,505 A | 10/1998 | Tolstoshev et al. |
| 6,103,502 A | 8/2000 | Möller et al. |
| 6,150,133 A | 11/2000 | Mead et al. |
| 7,202,059 B2 * | 4/2007 | Habermann et al. ......... 435/69.7 |
| 2002/0173620 A1 | 11/2002 | Habermann |
| 2003/0176673 A1 * | 9/2003 | Habermann ................ 536/23.1 |

FOREIGN PATENT DOCUMENTS

| AU | 726264 | 12/1997 |
| DE | 3430556 A1 | 2/1986 |
| DE | 10033195 A1 | 3/2002 |
| EP | 0 158 564 A1 | 10/1985 |
| EP | 0 195 691 B1 | 9/1986 |
| EP | 0 214 826 B1 | 3/1987 |
| EP | 0 324 712 B1 | 7/1989 |
| EP | 0 347 781 B1 | 12/1989 |
| EP | 0 375 437 B1 | 6/1990 |
| EP | 0 419 504 B1 | 4/1991 |
| EP | 0 448 093 B1 | 9/1991 |
| EP | 0 468 539 B1 | 1/1992 |
| EP | 0 489 780 B1 | 6/1992 |
| EP | 0 511 393 A1 | 11/1992 |
| EP | 0 549 915 B1 | 7/1993 |
| EP | 0 200 655 B1 | 4/1995 |
| EP | 0 678 522 B1 | 10/1995 |
| EP | 0 775 710 A1 | 5/1997 |
| WO | WO 91/09125 | 6/1991 |
| WO | WO 92/00321 | 1/1992 |
| WO | WO 01/21662 A1 | 3/2001 |
| WO | WO 02/04486 | 1/2002 |
| WO | WO 02/04486 A2 | 1/2002 |

OTHER PUBLICATIONS

Branden et al. "Introduction to Protein Structure", Garland Publishing Inc., New York, 1991, p. 247.*
Rudinger J., Characteristics of amino acids a components of peptide hormone seqeunces, University Park Press, Baltimore, 1994., pp. 1-7.*
Bowie, et al., Deciphering the message in protein seqeunces: tolerance to amino acid substituions (1990) Science, vol. 247 : pp. 1306-1310.*
Dé et al., "Channel-forming properties and structural homology of major outer membrane proteins from *Pseudomonas fluorescens* MFO and OE 28.3," *FEMS Microbiology Letters*, 127, 267-272, 1995.
Fürste et al, "Molecular cloning of the plasmid RP4 primase region in a multi-host-range *tacP* expression vector," *Gene*, 48(1), 119-131, 1986.
Griessbach et al., "Assay of Hirudin in Plasma Using a Chromogenic Thrombin Substrate," *Thrombosis Research*, 37, 347-350, 1985.
Price et al., "Expression, purification and characterization of recombinant murine granulocyte-machrophage colony-stimulating factor and bovine interleukin-2 from yeast," *Gene*, 55(2-3), 287-293, 1987.
Rioux et al., "Genes on the 90-Kilobase Plasmid of *Salmonella typhimurium* Confer Low-Affinity Cobalamin Transport: Relationship to Fimbria Biosynthesis Genes," *Journal of Bacteriology*, 172(11), 6217-6222, 1990.

(Continued)

*Primary Examiner*—Karen Cochrane Carlson
*Assistant Examiner*—Rosanne Kosson

(57) ABSTRACT

A nucleic acid sequence including: $P_x$-$S_x$-$B_n$-(ZR)-transport peptide-$(Z_1Z_2)$-protein(Y)-$(Z_1Z_2)$-protein($Y_m$)-T. The nucleic acid codes for a fusion protein including a peptide encoded by transport peptide linked via a peptide encoded by a first $Z_1Z_2$ to a protein encoded by protein(Y) which in turn is linked to T when m equals zero, or when m does not equal zero, is linked to a peptide encoded by a second $Z_1Z_2$ which is linked to a chain comprising at least one and up to 5 proteins encoded by protein($Y_m$) which either correspond to the protein encoded by protein(Y) or can be different from the protein encoded by protein(Y). The peptide encoded by transport peptide improves the rate of secretion of the protein encoded by protein(Y) and the protein encoded by protein($Y_m$), when the protein encoded by protein($Y_m$) is present. Proteins thereof, host cells thereof, and processes thereof.

9 Claims, No Drawings

OTHER PUBLICATIONS

Rosenfeld et al., Production and Purification of Recombinant Hirudin Expressed in the Methylotrophic Yeast *Pichia pastoris, Protein Expression and Purification*, 8(4), 476-482, 1996.

Shuttleworth et al., "Sequence of the gene for alkaline phosphatase from *Escherichia coli* JM83," *Nucleic Acids Research*, 14(21), 8689, 1986.

Wetekam et al., "The nucleotide sequence of cDNA coding for preproinsulin from the primate *Macaca fascicularis*," *Gene*, 19(2), 179-183, 1982.

Weydemann et al., "High-level secretion of hirudin by *Hansenula polymorpha*—authentic processing of three different preprohirudins," *Applied Microbiology and Biotechnology*, 44(3-4), 377-385, 1995.

Winter et al., "Increased Production of Human Proinsulin in the Periplasmic Space of *Escherichia coli* by Fusion to DsbA," *Journal of Biotechnology*, 84, 175-185 (2000).

Thim et al., "Secretion and Processing of Insulin Precursors in Yeast," *Proc. Natl. Acad. Sci.*, 83: 6766-6770 (1986).

On-line Medical Dictionary—definition of signal sequence http://cancerweb/ncl.ac.uk.

Bio Critical Synergy, The Biotechnology Industry and Intellectual Property Organization Presentation, Oct. 17, 1994, pp. 75-107.

Merriam-Webster On-Line Dictionary, http://www.m-w.com/cgi-bin/, definition of fermentation and supernatant.

Rothblatt et al., Secretion in yeast: structural features influencing the post-translational translocation of prepro-alpha-factor in vitro, EMBO J. 1987, pp. 3455-3463, vol. 6.

Bischoff et al., Isolation of recombinant hirudin by preparative high-performance liquid chromatography, J of Chromatography, 1989, pp. 245-255, vol. 476.

\* cited by examiner

```
                        SEQUENCE LISTING

<160> NUMBER OF SEQ ID NOS: 13

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence:hir_insfkr

<400> SEQUENCE: 1
atccctgagg aataccttca gaagcgattt gttaaccaac acttgtgtgg              50

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:protein
      hir_insfkr

<400> SEQUENCE: 2

Ile Pro Glu Glu Tyr Leu Gln Lys Arg Phe Val Asn Gln His Leu Cys
  1               5                  10                  15

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence:hir_insrevkr
```

<400> SEQUENCE: 3
cctcacaagt gttggttaac aaatcgcttc tgaaggtatt cctcagggat    50

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence:hirf1

<400> SEQUENCE: 4
tttttttgga tcctttggat aaaagactta cgtatactga ctgcac    46

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:protein hirf1

<400> SEQUENCE: 5

Leu Thr Tyr Thr Asp Cys
 1               5

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:insnco1rev

<400> SEQUENCE: 6 tttttttccat gggtcgacta tcag    24

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:B_KR_Af1

<400> SEQUENCE: 7
cttctacact ccaaagacga aacgcggtat cg    32

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:B_KR_Arev1

<400> SEQUENCE: 8
caacattgtt caacgatacc gcgtttcgtc ttt    33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:insncorev

<400> SEQUENCE: 9 tttttttccat ggtcatgttt gacagcttat cat    33

```
<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence:hir_insfkr

<400> SEQUENCE: 10
atccctgagg aataccttca gaagcgattt gtgaaccagc acctgtgcgg c          51

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence:hir_insrevkr

<400> SEQUENCE: 11
gccgcacagg tgctggttca caaatcgctt ctgaaggtat tcctcaggga t          51

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:pichia_H_lf1

<400> SEQUENCE: 12 ttttttctc gagaaaagac ttacgtatac tgac                              34

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence:pichia_H_
      lrev2

<400> SEQUENCE: 13
tttttggcgc cgaattcact attagttaca gtagttttcc                       40
```

NUCLEIC ACIDS ENCODING A HIRUDIN AND PRO-INSULIN AS SUPERSCRETABLE PEPTIDES AND FOR PARALLEL IMPROVEMENT OF THE EXPORTED FORMS OF ONE OR MORE POLYPEPTIDES OF INTEREST

CROSS-REFERENCE TO RELATED APPLICATIONS

This application claims priority under 35 U.S.C. §119(e) of U.S. Provisional Application No. 60/270,592, filed Feb. 23, 2001, the disclosure of which is expressly incorporated by reference herein in its entirety, and also claims priority under 35 U.S.C. §119 of German Application No. 101 08 100.6, filed Feb. 20, 2001, the disclosure of which is expressly incorporated by reference herein in its entirety.

DESCRIPTION OF THE INVENTION

In view of economic viability, processes for the production of pharmaceutically relevant proteins must lead to biologically active products of the highest possible purity. The expression of such relevant proteins in yeasts is widely used for this purpose. The production of proteins such as insulin, GM-CSF (LEUKINE®) and hirudin derivatives like lepirudin (REFLUDAN®), is an example of the successful development of genetic engineering processes which are based on the synthesis of the particular protein or precursors thereof in yeast. Generally, yeasts can directly synthesize hirudins with good yields which are on the gram scale when using *Hansenula polymorpha* (Weydemann et al., Appl. Microbiol Biotechnol. 44: 377-385, 1995) or *Pichia pastoris* (Rosenfeld et al., Protein Expr. Purif: 4, 476 -82, 1996).

EP-A 0 324 712 describes a hirudin derivative (REFLUDAN®) whose N-terminal amino acid is leucine and its constitutive expression in *Saccharomyces cerevisiae* strain Y79. EP-A 0 347 781 describes mini-proinsulin and, by way of example, its expression in bakers' yeast. REFLUDAN® and insulin are produced by carrying out two separate expressions.

Surprisingly, we have now found that hirudin derivatives and mini-proinsulin derivatives can be obtained from a common precursor protein by fusing the precursor protein to a signal or leader sequence, which is recognized by yeasts as a secretion signal, via a basic dipeptide, such as Lys-Arg, and likewise introducing between the N-terminal hirudin derivative and the mini-proinsulin derivative a cleavage site which is recognized by a yeast endoprotease. Here too, preference is given to a basic dipeptide, for example Lys-Arg. After expression, a hirudin derivative extended by Lys-Arg and the mini-proinsulin derivative starting with the first amino acid of the insulin B chain are found in the supernatant. Surprisingly, we have found here that the yield of mini-proinsulin markedly improves compared with the yield achievable by direct signal—mini-proinsulin expression, whereas the yield of the hirudin derivative remains nearly the same. Surprisingly, hirudin thus acts as a kind of enhancer peptide with respect to the yield of mini-proinsulin.

Peptides which can act as enhancer proteins are usually those which are relatively small and which are secreted naturally in large amounts over a short period, for example from glandular tissue. Peptides of this type, which include, for example, snake venom or eglin C or TAP (tick anticoagulant peptide), are distinguished by extremely good export compatibility. The invention relates to such proteins.

Another advantage may result from the hirudin derivative having equal or better pharmaceutical properties compared with hirudin which is already used in pharmaceuticals. In this case, it becomes possible to produce two or even more pharmaceuticals from one fermentation. As a consequence, less fermentation capacity is required. This is directly beneficial to production costs.

However, the production of a plurality of products is optional. The amount of needed REFLUDAN®, for example, is less than that of insulin, and this may result in processes in which one of the pharmaceutically interesting substances is discarded.

To improve the yield, it is possible, as suggested in EP-A 0 200 655, to place a short peptide sequence between the signal or leader sequence and Lys-Arg at the amino terminus of the hirudin derivative, as a linker to the signal or leader sequence. The choice of signal or leader sequence directly affects the yield of the protein of interest. The selection of such a sequence is the subject of further optimizations. The sequence located at the 3' end of the expression cassette, too, directly affects the yield by influencing mRNA stability. Here too, the sequence can be optimized for each protein of interest to be expressed. This is also true for the choice of a suitable promoter, which can be inducible or constitutively active. The choice of vector system and host system is equally important for the yield. Thus, instead of bakers' yeast which has been used by way of example, it is also possible to use the yeasts *Pichia pastoris, Hansenula polymorpha* or *Kluyveromyces lactis* together with vectors or expression cassettes, which have in each case been optimized for the different physiology of the host cell.

Another advantage of processes allowing secretion into the medium is the simpler protein-chemical workup of the protein of interest. Surprisingly, we have found that mini-proinsulin can be concentrated in the presence of hirudin by filtration through membranes having an exclusion limit for molecules with a molecular weight of greater than 10 kDa. The mini-proinsulin and hirudin are found almost exclusively in the retentate. The development of novel separation techniques and new combinations of process steps makes it possible to improve purification processes. This is directly beneficial to the yield and therefore to production costs.

The invention thus may relate to a DNA-molecule of the form:

$P_x$-$S_x$-$B_n$-(ZR)-transport peptide-($Z_1Z_2$)-protein(Y)-($Z_1Z_2$)-protein($Y_m$)-T;

wherein the expression cassette codes for a fusion protein comprising a peptide encoded by transport peptide linked via a peptide encoded by a first $Z_1Z_2$ to a protein encoded by protein(Y) which in turn is linked via a peptide encoded by an optional second $Z_1Z_2$ which, when m does not equal zero, is linked to a chain comprising at least one and up to 5 proteins encoded by protein($Y_m$) which either correspond to the protein encoded by protein(Y) or can be different from the protein encoded by protein(Y) and the peptide encoded by transport peptide improves the rate of secretion of the protein encoded by protein(Y) and improves the rate of secretion of the protein encoded by protein($Y_m$) when the protein encoded by ($Y_m$) is present, where:

$P_x$ is any promoter DNA sequence selected in such a way that optimal yields of the protein of interest become obtainable;

$S_x$ is any DNA which, accordingly, encodes any signal or leader sequence which allows optimal yields;

$B_n$ is 1-15 genetically encoded amino acids or a chemical bond;

Z is the codon of an amino acid selected from Lys and Arg;

$Z_1$ is the codon of an amino acid selected from Lys and Arg;

$Z_2$ is the codon of an amino acid selected from Lys and Arg;

R is an Arg codon;

transport peptide is a DNA sequence encoding a peptide which can be transported efficiently and which can pass membranes, such as hirudin or a hirudin derivative, for example;

protein(Y) is a DNA sequence encoding any protein which can be produced and secreted by yeast;

protein($Y_m$) is a DNA sequence encoding any protein which can be produced and secreted by yeast (m=1-5) or is a chemical bond (m=0);

T is an untranslated DNA sequence advantageous to the expression.

Another aspect of the invention is a fusion protein encoded by any of the above-mentioned DNA molecules.

A further aspect of the invention is a multicopy vector or a plasmid comprising the above-mentioned DNA-molecule.

An additional aspect of the invention is a host cell comprising the above-mentioned DNA-molecule, or the above-mentioned multicopy vector or the above-mentioned plasmid, as a part of its chromosome, as a part of a mini-chromosome, or extra-chromosomally, wherein preferentially said host cell is a yeast, in particular selected from *Saccharomyces cerevisiae, Kluyveromyces lactis, Hansenula polymorpha* and *Pichia pastoris*.

Another aspect of the invention is a process of fermenting the above-mentioned proteins, in which
(a) the above-mentioned DNA-molecule, the above-mentioned multicopy vector, or the above-mentioned plasmid is expressed in an above-mentioned host cell, and
(b) the expressed proteins are isolated from the supernatant of the cell culture.

For instance, after completion of expression by fermentation, the pH may be adjusted to about 2.5-3.5 in order to precipitate non-desired proteins and the expressed proteins are isolated from the supernatant of the precipitation.

Another aspect of the invention is the above mentioned process, in which process after separating the fermentation supernatant from the host cells, the host cells are repeatedly cultured in fresh medium, and the released fusion protein is isolated from each supernatant obtained during cultivation.

Another aspect of the invention is the above mentioned process, wherein a process step for concentrating the expressed protein in the supernatant after precipitation is selected from microfiltration, hydrophobic interaction chromatography, and ion exchange chromatography.

An additional aspect of the invention is a process for preparing insulin, in which
(a) proinsulin may be encoded by protein(Y) of the above-mentioned expression cassette in the above-mentioned process;
(b) the proinsulin of step (a) is isolated and treated with trypsin and carboxypeptidase B; and
(c) insulin is isolated from the reaction mixture of step (b), For example, transport peptide may encode for hirudin or hirudin derivative which is destroyed or biologically inactivated after step (a) or (b).

A further aspect of the invention is a protein wherein the protein is a hirudin-derivative with two basic amino acid residues at its C-terminal end.

Leeches of the type Hirudo have developed, for example, various isoforms of the thrombin inhibitor hirudin. Hirudin has been optimized for pharmaceutical requirements by artificial variation of the molecule, for example exchange of the N-terminal amino acid (e.g., EP 0 324 712). The invention includes the use of hirudin and hirudin variants. Particular aspects of the invention use one of the natural hirudin isoforms (the natural isoforms are together denoted "hirudin"). A natural isoform is, for example, Val-Val-hirudin or Ile-Thr-hirudin. Other aspects of the invention use a variant of a natural hirudin isoform. A variant is derived from a natural hirudin isoform but contains, for example, additional amino acids and/or amino acid deletions and/or amino acid exchanges compared with the natural isoform. A hirudin variant may contain alternating peptide segments of natural hirudin isoforms and new amino acids. Hirudin variants are known and are described, for example, in DE 3 430 556. Hirudin variants are commercially available in the form of proteins (Calbiochem Biochemicals, cat. no. 377-853, -950, -960). The term "hirudin derivative" denotes sequences which are at least 40%, homologous to a natural hirudin isoform, such that 40% of the total amount of the 65 amino acids known from lepirudin should be found within the variant The hirudin derivative may be even more homologous than 40%, such as at least about 60%, or at least about 80%, homologous to a natural hirudin isoform. The % homology is calculated by the Compare Program, which is available from the Wisconsin Package distributed by the Genetics Computer Group; 575 Science Drive; Madison, Wis.

The expression cassette may be introduced into a yeast such as *S. cerevisae, K. lactis, H. polymorpha* or *P. pastoris*. Said expression cassette may have one or more copies stably integrated into the particular yeast genome or may be present extrachromosomally on a multicopy vector. This technique is also applicable to other systems such as animal cell culture or plant cells. This technique is also a subject of the invention.

In accordance with one aspect, the present invention is directed to a nucleic acid sequence comprising: $P_x$-$S_x$-$B_n$-(ZR)-transport peptide-($Z_1Z_2$)-protein(Y)-($Z_1Z_2$)-protein($Y_m$)-T. The nucleic acid codes for a fusion protein comprising a peptide encoded by transport peptide linked via a peptide encoded by a first $Z_1Z_2$ to a protein encoded by protein(Y), which is linked to T when m equals zero, or when m does not equal zero, is linked to a peptide encoded by a second $Z_1Z_2$ which is linked to a chain comprising at least one and up to 5 proteins encoded by protein($Y_m$), which either correspond to the protein encoded by protein(Y) or can be different from the protein encoded by protein(Y). The peptide encoded by transport peptide improves the rate of secretion of the protein encoded by protein(Y) the protein encoded by protein($Y_m$), when the protein encoded by ($Y_m$) is present. $P_x$ comprises a promoter sequence. $S_x$ comprises a nucleic acid sequence encoding a signal or leader sequence. $B_n$ is 1 to 15 codons, when n is an integer from 1 to 15, or a chemical bond, when n is zero. Z is a codon for lysine or arginine. R is an arginine codon. Transport peptide comprises a nucleic acid sequence encoding a peptide that is transported efficiently across membranes. $Z_1$ is a codon for lysine or arginine. $Z_2$ is a codon for lysine or arginine. Protein($Y_m$) comprises a nucleic acid sequence encoding at least one and up to 5 proteins that are produced and secreted by yeast when m is an integer from 1 to 5, or is a chemical bond when m=0. Protein (Y) comprises a nucleic acid sequence encoding a protein that is produced and secreted by yeast and whose biological activity, when protein($Y_m$) is not a chemical bond, is not impaired by a basic dipeptide extension encoded by $Z_1Z_2$ or allows degradation of the basic dipeptide extension by carboxypeptidase. T is an untranslated expression-enhancing nucleic acid sequence.

Transport peptide may encode for hirudin or hirudin derivative.

Protein(Y) may encode for one of mini-proinsulin (EP-A 0 347 781), naturally found proinsulin, proinsulin derivative, interleukin, lymphokine, interferon, blood clotting factor, blood clotting factor derivative.

The term "proinsulin derivative" denotes sequences which are at least 60% homologous to a sequence of a naturally occurring proinsulin. It is understood that the term insulin defines a polypeptide composed out of a B- and A-chain. The homology of the proinsulin derivative may be even higher, such as at least about 60%, or at least about 80%, homologous to a sequence of a naturally occurring proinsulin. The homology is calculated by the Compare Program, which is available from the Wisconsin Package distributed by the Genetics Computer Group; 575 Science Drive; Madison, Wis. The homology does not cover the C-peptide, which can be via genetic engineering totally different from any naturally found C-peptide. The term "blood clotting factor derivative" denotes sequences which are muteins of a natural factor, but which are either advantageous in respect of the production process or in respect of pharmacological characteristics and which are at least 70% homologous to a naturally occurring blood clotting factor. The homology of the blood clotting factor derivative may be even higher, such as at least about 80%, or at least about 90%, homologous to a naturally occurring blood clotting factor. The above % homologies are calculated as described above.

In another aspect, the present invention is directed to a fusion protein encoded by the nucleic acid of the invention.

The fusion protein may comprise hirudin-derivative with two basic amino acid residues at its C-terminal end.

In still another aspect, the present invention is directed to a multicopy vector comprising the nucleic acid of the invention.

In yet another aspect, the present invention is directed to a plasmid comprising the nucleic acid of the invention.

In a further aspect, the present invention is directed to a host cell comprising the nucleic acid of the invention as a part of the host cell chromosome, as a part of a mini-chromosome, or extra-chromosomally.

The host cell may be a yeast which may be selected from *Saccharomyces cerevisiae, Kluyveromyces lactis, Hansenula polymorpha*, and *Pichia pastoris*.

In another aspect, the present invention is directed to a host cell comprising the multicopy vector of the invention.

In still another aspect, the present invention is directed to a host cell comprising the plasmid of the invention.

In a further aspect, the present invention is directed to a process of fermentative production of protein, comprising: expressing the nucleic acid of the host cell of the invention to form the fusion protein in a supernatant of a cell culture; and isolating the fusion protein from the supernatant of the cell culture.

After expressing the nucleic acid, isolating the fusion protein may comprise adjusting a pH of the cell culture to about 2.5 to 3.5 to precipitate non-desired protein.

The process may further comprise separating the supernatant from the host cell, and after separating the supernatant from the host cell, the host cell may be repeatedly cultured in fresh medium to form additional supernatant from each culture, and the fusion protein may be isolated from each additional supernatant.

The isolating of the fusion protein may comprise precipitating the fusion protein from the supernatant, the process further comprising removing the protein encoded by protein (Y) from the fusion protein, and concentrating the protein encoded by protein(Y) by one of microfiltration, hydrophobic interaction chromatography, and ion exchange chromatography.

In another aspect, the present invention is directed to a process for preparation of insulin, comprising: obtaining fusion protein by one of the above processes, wherein the protein encoded by protein(Y) comprises proinsulin; releasing proinsulin into a reaction mixture by treating the fusion protein with trypsin and carboxypeptidase B; and isolating insulin from the reaction mixture.

Transport peptide may encode for hirudin or hirudin derivative. The hirudin or hirudin derivative may be destroyed or biologically inactivated after the releasing of the prosinsulin or the isolating of the insulin.

The expression system described below serves as an example. In order to introduce the expression cassette into said selected system, the appropriate recombinant DNA constructs may be made depending on the type of host system selected. Accordingly, industrial fermentation can be optimized in relation to the selected host/vector system.

In view of the above, the following examples which are not intended to be restrictive describe the invention in more detail.

EXAMPLE 1

Construction of a Yeast Expression Plasmid Encoding Hirudin (REFLUDAN®)-Lys-Arg-mini-proinsulin Starting materials were the plasmids pK152 (PCT/EP00/08537, which is incorporated by reference herein in its entirety), pSW3 (EP-A 0 347 781, which is incorporated by reference herein in its entirety) and the recombinant yeast plasmid derivative coding for bovine interleukin 2, which was pαADH2 plus the cDNA for IL2 (Price et al., Gene 55, 1987, which is incorporated by reference herein in its entirety). The yeast plasmid was distinguished by the fact that it carries the α factor leader sequence under the control of the yeast ADH2 promoter. This sequence was followed by the bovine interleukin 2 cDNA sequence which was connected via a KpnI restriction enzyme recognition site and which contained an NcoI restriction enzyme recognition site in the untranslated 3' end which was unique in the vector. Thus, the cDNA sequence was readily removable from the plasmid via KpnI/NcoI cleavage. Since good expression yields were reported, it was assumed that the remaining 3' interleukin 2 sequence (as a terminator sequence) had a stabilizing effect on the mRNA and thus need not be deleted or replaced by a yeast terminator sequence. Plasmid pK152 carried the DNA sequence coding for Leu-hirudin (REFLUDAN®) and plasmid pSW3 carried the DNA sequence for mini-proinsulin. The gene sequence which was to encode hirudin-Lys Arg-mini-proinsulin was first prepared by means of PCR technology. For this purpose, 4 primers were prepared with the aid of the EXPEDITE™ DNA synthesis system:

```
1 i. hir_insfkr (SEQ ID NO:1, encoded protein segment: SEQ ID
NO:2)

I   P   E   E   Y   L   Q   K   R   F   V   N   Q   H   L   C
5'-ATCCCTGAGGAATACCTTCAGAAGCGATTTGTTAACCAACACTTGTGTGG-3'
    59  60  61  62  63  64  65        B1  B2  B3  B4  B5  B6  B7 ii. hir_in srevkr (SEQ ID NO:3)
5'-CCTCACAAGTG TTGGTTAACA AATCGCTTCT GAAGGTATTC CTCAGGAT-3' iii. hirf1 (SEQ ID NO:4, encoded protein segment: SEQ ID NO:5)

L   T   Y   T   D   C
5'-TTTTTTTGGATCCTTTGGATAAAAGACTTACGTATACTGACTGCAC iv. insncol rev (SEQ ID NO:6)
5'-TTTTTTCCAT GGGTCGACTATCAG-3'
```

Primer hir_insfkr described the junction between codons for the terminal amino acids of hirudin (59-65) and the insulin sequence B1-B7 via the Lys-Arg linker. Primer hir_insrevkr was 100% complementary thereto. Primer hirf1 coded for the start of the hirudin gene extended to the Kpnl cleavage site as described in EP-A 0 324 712, which is incorporated by reference herein in its entirety. Primer insnco1rev marked the 3' end of the synthetic mini-proinsulin according to EP-A 0 347 781, which is incorporated by reference herein in its entirety. Two standard polymerase chain reactions were carried out using the primer pairs hirf1/hir_insrevkr with DNA of plasmid pK152 as template and hir_insfkr/insnco1rev with DNA of plasmid pSW3 as template. The reactions were carried out in 100 µl of PCR buffer (provided by the Advantage-HFTM PCR Kit tk(Clontech Cat' 1909-1)) with, in each case, 200 nmol of each primer, 1 µl of polymerase (provided by the kit) and 100 ng of vector. Step 1 was a 2-minute incubation at 95° C. This was then followed by 25 cycles of 30" at 95° C., 30" at 55° C. and 30" at 72° C. The last cycle was followed by an incubation at 72° C. for 3 minutes, and the reaction was subsequently stopped.

Since the primers hir_insrevkr and hir_insfkr were 100% complementary, the DNA products of the two reactions overlapped according to said sequence so that in a third reaction (under the same conditions as described above), using 5% of each of the generated PCR fragments of the first two reactions as templates and the primers hirf1 and insnco1rev in one reaction, a DNA fragment was formed, which encoded hirudin and mini-proinsulin separated by Lys-Arg. The PCR fragment was digested (according to the manufacturer's protocol) by the enzymes Kpnl und Ncol and then, in a T4 ligase reaction (according to the manufacturer's protocol), inserted into the pαADH2 vector opened by Kpn1/Ncol. In the same manner, except as noted below, as Example 7 of EP-A 0 347 781, which is incorporated by reference herein in its entirety, competent *Escherichia coli* strain MM294 cells were then transformed with the ligation mixture. Plasmid DNA was then isolated from two clones for characterization by means of DNA sequence analysis by standard techniques. After confirmation of the inserted DNA sequence, DNA of a plasmid preparation was used to transform cells of bakers' yeast strain Y79, according to said Example 7. However, when using the pαADH2 vector, introduction of the vector was followed by selecting for complementation of the trp1-1 mutation on yeast minimal medium agar plates, which contained no tryptophan, in contrast to said Example 7. For another control, plasmid DNA was reisolated from yeast transformants and analyzed by means of restriction analysis. The expression vector constructed was denoted pADH2Hir_KR_Ins. Expression was carried out according to Example 4 of the present document.

EXAMPLE 2

Construction of a Yeast Expression Plasmid Encoding Hirudin (Refludan®)-Lys-Arg-insulin B chain-Lys-Arg-insulin A chain Patent application EP-A 0 195 691, which is incorporated by reference herein in its entirety, described proinsulin derivatives which can contain the dipeptide XY, where X and Y each correspond to either Lys or Arg, as a linker between the B and A chains of insulin. The present Example describes the preparation of an expression vector for proinsulin derivatives of this kind. A DNA sequence which coded for a proinsulin derivative of the form B chain-Lys-Arg-A chain was selected by way of example and synthesized accordingly.

As described in more detail below, the synthesis of the gene segment was carried out similar to Example 1 of the present document. The oligonucleotide sequences used included hirF1 and insnco1rev. The oligonucleotides B_KR_Af1 and B_KR_Arev1 were synthesized for this Example.

```
B_KR_Af1 had the sequence (SEQ ID NO:7)
5'-CTTCTACACTCCAAAGACGAAACGCGGTATCG-3'

B_KR_Arev1 had the sequence (SEQ ID NO:8)
5'-CAACATTGTTCAACGATACCGCGTTTCGTCTTT-3'
```

The part shown in bold type of the two primers depicted indicates the partially overlapping sequence. Both primers paired exactly with the sequence of the mini-proinsulin gene of EP-A 0 347 781, which is incorporated by reference herein in its entirety, apart from the 6 underlined nucleotides. The underlined part corresponds to codons for Lys and Arg. DNA of the plasmid pADH2Hir_KR_Ins constructed according to Example 1 of the present document served as template in the PCR.

As described in Example 1, two polymerase chain reactions (under the same conditions as Example 1, except as noted below) were carried out using the primer pairs hirf1/B_KR_Arev1 and insnco1rev/B_KR_Af1. The template in each case was DNA of the plasmid pADH2Hir_KR_Ins constructed in Example 1. The products of both reactions served as template in a third PCR (under the same conditions as Example 1) using the primer pair hirf1 and insnco1. The reaction product from the third PCR was cleaved with Ncol/Sall and inserted into the opened pαADH2 vector. After sequence and restriction analysis by standard techniques, the correct plasmid was referred to as pADHHirKR_B_KR_A.

EXAMPLE 3

Construction of a Yeast Plasmid Coding for Hirudin-Lys-Arg-simian Proinsulin

Patent application EP-A 489 780, which is incorporated by reference herein in its entirety, describes a plasmid, pINT90d, which contains cDNA encoding simian proinsulin (Wetekam et al., Gene 19, p.179-183, 1982, which is incorporated by reference herein in its entirety). DNA of said plasmid and DNA of plasmid pK152 served as templates. The primer hirf1 described in Example 1 of the present document was used and three further primers were synthesized.

Primer insncorev reversely bound to the 3' region of the insulin gene cloned in pINT90d and had the sequence:

5'-TTTTTTCCATGGTCATGTTTGACAGCT-TATCAT-3' (SEQ ID NO: 9)

The underlined sequence indicates the recognition site for the restriction enzyme Ncol.

Primer hir_insfkr had the sequence:

5'-ATCCCTGAGG AATACCTTCA GAAGCGATTT GTGAACCAGC ACCTGTGCGG C-3' (SEQ ID NO: 10)

Here, the nucleotides in bold type indicate the Lys-Arg linker between hirudin and proinsulin.

Primer hir_insrevkr was completely complementary to primer hir_inskr and had the sequence:

5'-GCCGCACAGG TGCTGGTTCA CAAATCGCTT CTGAAGGTAT TCCTCAGGGA T-3' (SEQ ID NO: 11)

Corresponding to Example 1, two polymerase chain reactions were carried out under the same conditions as Example 1, except with different primers and templates. The primer pair hirf1/hir_insrevkr was reacted with DNA of plasmid pK152 and the primer pair hir_insfkr/insncorev was reacted with DNA of plasmid pINT90d. As described in Example 1, the products of both reactions served as templates in a third PCR (under the same conditions as in Example 1) using the primer pair hirf1/insncorev. The DNA product of this reaction included the sequence for hirudin-Lys-Arg-proinsulin. It was subsequently cleaved with the enzymes NcoI and KpnI and, corresponding to Example 1, inserted into the plasmid pαADH2. Accordingly, expression vector for any natural proinsulin derivatives may be constructed.

EXAMPLE 4

Expression of the Recombinant Products

The expression was divided into two phases. First, a preculture was cultivated in yeast minimal medium. The culture was grown overnight in a incubation shaker at 30° C. and 240 rpm. The yeast minimal medium had the following composition per 1 liter:

| | |
|---|---|
| 6.7 g | yeast nitrogen base (without amino acids) |
| 5.0 g | casamino acids (vitamin-free) |
| 0.008% | adenine |
| 0.008% | uracil |
| 2% | glucose |

As described in more detail below, the main or expression culture was inoculated with an aliquot of the preculture.
The main culture medium contained per liter:

| | |
|---|---|
| 10 g | yeast extract |
| 20 g | peptone |
| 0.008% | adenine |
| 0.008% | uracil |
| 4% | glucose |

Using the media described, expression was carried out in a shaken flask in the following way: 0.3 ml of preculture which had been cultivated overnight was diluted with 80 ml of prewarmed main culture medium and incubated with vigorous shaking at 30° C. for approximately 24 hours. In each case, 1 ml of the culture produced in this way was then centrifuged, after determining the optical density, and, after removing the cells, the supernatant was lyophilized and analyzed by means of SDS-PAGE. The biologically active hirudin content was determined by carrying out a thrombin inhibition assay in accordance with Example 5 below.

An alternative fermentation protocol, which was not conducted as part of this Example, provides for the cells to be removed by filtration using filtration cassettes provided by Millipore or careful centrifugation at 3 to 5000×g. While isolating the protein of interest from the medium, the cells were provided with fresh prewarmed main culture medium in an amount of equal volume as the original main culture medium containing 1% ethanol and not more than 0.5% glucose as carbon source, and thus fermentation was continued without interruption. This step can be repeated up to 5 times.

EXAMPLE 5

Thrombin Inhibition Test

The hirudin concentration was determined according to the method of GrieRbach et al. (Thrombosis Research 37, pp. 347-350, 1985, which is incorporated by reference herein in its entirety). For this purpose, REFLUDAN®. standard was included in the measurements in order to establish a calibration curve from which the yield in mg/l was determined directly.

EXAMPLE 6

Cloning and Expression of the Hirudin-Lys-Arg-mini-proinsulin Fusion Protein in the *Pichia Pastoris* System INVITROGEN®. sells a cloning and expression kit for preparing recombinant proteins using *P. pastoris* as a host system. For this, a detailed technical protocol regarding preparation and subsequent expression of a *P. pastoris* system for the production of a desired recombinant protein is provided so that only the construction of the expression vector encoding the desired protein has to be described when following said protocols. The EASYSELECT™ Pichia expression kit (catalog no. K1740-01) was used.

The pPICZαA vector was part of the kit. Opening the vector by the restriction enzymes XhoI and SacII according to the manufacturer's protocol made it possible to append, similar to Example 1, a protein of interest to the alpha factor leader sequence and to test by means of SDS-PAGE analysis for secretion into the supernatant. Cloning required two primers. Primer pichia_H_If1 (SEQ ID NO: 12) had the sequence:

```
5'-TTTTTTTCTCGAGAAAAGA CTTACGTATACTGAC-3'
        XhoI         Hir₁ Hir₂ etc.
``` primer Pichia_H_lrev2 (SEQ ID NO: 13) had the sequence:

```
5'-TTTTTGGCGCCGAATTCACTATTAGTTACAGTAGTTTTCC-3'
        SacII EcoRI        A21
```

The template used was DNA of plasmid pADH2Hir_KR_Ins of Example 1. A standard PCR (under the conditions as described in Example 1) with both primers produced a DNA product which contained the sequence hirudin-Lys-Arg-mini-proinsulin extended by the XhoI and SacII integration sites. When the DNA product was cleaved appropriately and the fragment was isolated, said fragment was inserted into the opened vector DNA in a T4 DNA ligase reaction. In deviation from the manufacturer's protocol, *E. coli* strain MM294, described in Example 1, was transformed with the ligation mixture and recombinant colonies were screened for on zeocine selection plates. Plasmid DNA was reisolated from clones and then characterized by means of restriction and DNA sequence analysis. Using the plasmid constructed in this way, a *P. pastoris* expression clone for production of the peptides was then prepared by following the manufacturer's instructions.

EXAMPLE 7

Purification of Mini-proinsulin and Hirudin Using Hydrophobic Interaction Chromatography The purification requires separation of the two proteins of the fusion protein at an early stage. The fusion protein is processed to REFLUDAN®-LysArg and mini-proinsulin by the natural yeast protease system. After completion of the expression of Example 6, the medium is analyzed by means of analytical RP-HPLC. In contrast to most other polypeptides found in the supernatant due to either spontaneous lysis of yeast cells or secretion, the two proteins, hirudin and mini-proinsulin, are not precipitated at pH 2.5-3. The culture medium is therefore acidified appropriately, using concentrated H$_2$SO$_4$, to pH 2.5-3.5 and then, after completion of the precipitation which takes at least 2 hours, the precipitate and the cells are removed by centrifugation. After centrifugation, the medium is adjusted using NaOH to pH 3.5-7 and the two components hirudin and mini-proinsulin are separated from one another by means of hydrophobic interaction chromatography, for example by using a chromatography column filled with Diaion HP20® material as described in EP-A 0 347 781, which is incorporated by reference herein in its entirety. Hirudin can then be isolated from the hirudin-containing fractions according to EP-A 0 549 915, which is incorporated by reference herein in its entirety, and insulin can be isolated from the mini-proinsulin-containing fractions according to EP-A 0 347 781, which is incorporated by reference herein in its entirety.

EXAMPLE 8

Preparation of Insulin from Mini-proinsulin Using Ion Exchange Chromatography

At the end of the expression period, the culture medium is adjusted using concentrated H$_2$SO$_4$ to pH 6.8 and trypsin is then added with stirring so that a final concentration of 4-8 mg per liter is established. After incubation for approximately 4 hours, the fermentation broth treated in this way is adjusted using concentrated H$_2$SO$_4$ to pH 2.5-3. After 1-6 hours of precipitation, the precipitate is removed by centrifugation at greater than 5000×g. The mono-Arg-insulin formed is then isolated via ion exchange chromatography, by S-SEPHAROSE® in a buffer of 50 mM lactic acid and 30% (v/v) isopropanol (pH 3.5). Elution is carried out by means of an NaCl linear gradient of 0.05-0.5 M salt. The product-containing fractions are diluted 1:1 with H$_2$O and then ZnCl$_2$ is added, so that a 0.1% strength ZnCl$_2$ solution is formed. In this regard, the fractions are analyzed for insulin by SDS-PAGE analysis and by Western Blot analysis. For standard Western Blot experiments the polyclonal Guinea Pig Anti-insulin (Code NO.:A0564, DAKO Corp.) is used. Mono-Arg-insulin precipitates at pH 6.8 and is converted to insulin according to EP-A 0 324 712, which is incorporated by reference herein in its entirety.

EXAMPLE 9

Preparation of Insulin from Mini-proinsulin Using Filtration

At the end of the expression period of Example 6, cells and supernatant components are removed by precipitation at pH 2.5 to 3 and centrifugation as in Example 8. Then, the medium is concentrated via filtration through membranes having an exclusion limit of 10 kDa as described by EP-A-0 775 710. Like the hirudin derivative, mini-proinsulin is found quantitatively in the retentate and can then be processed to insulin according to Example 8.

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. A nucleic acid which comprises:
$P_x$—$S_x$-(ZR)-nucleic acid encoding a transport peptide-($Z_1Z_2$)-nucleic acid encoding a protein(Y)-T; wherein:
$P_x$ comprises a promoter;
$S_x$ comprises a nucleic acid encoding a signal or leader;
Z is a codon for lysine or arginine;
R is an arginine codon;
transport peptide comprises hirudin or lepirudin;
$Z_1$ is a codon for lysine or arginine;
$Z_2$ is a codon for lysine or arginine;
protein(Y) comprises a protein selected from the group consisting of mini-proinsulin and proinsulin; and
T is a terminator.

2. A multicopy vector comprising the nucleic acid of claim 1.

3. A plasmid comprising the nucleic acid of claim 1.

4. A host cell comprising the nucleic acid of claim 1 as a part of the host cell chromosome, as a part of a mini-chromosome, or extra-chromosomally.

5. The host cell of claim 4, wherein the host cell is a yeast.

6. The host cell of claim 5, wherein the yeast is selected from *Saccharomyces cerevisiae, Kluyveromyces factis, Hansenula polymorpha,* and *Pichia pastoris.*

7. A host cell comprising the multicopy vector of claim 2.

8. A host cell comprising the plasmid of claim 3.

9. The nucleic acid according to claim 1 wherein the hirudin is selected from the group consisting of Val-Val-hirudin and Ile-Thr-hirudin.

* * * * *

UNITED STATES PATENT AND TRADEMARK OFFICE
CERTIFICATE OF CORRECTION

PATENT NO. : 7,638,618 B2
APPLICATION NO. : 10/076631
DATED : December 29, 2009
INVENTOR(S) : Paul Habermann It is certified that error appears in the above-identified patent and that said Letters Patent is hereby corrected as shown below:

In column 7, line 55, delete "(Refludan®)" and insert -- (REFLUDAN®) --, therefor.

In column 8, line 2, delete "hirF1" and insert -- hIRF1 --, therefor.

In column 9, line 67, delete "REFLUDAN®." and insert -- REFLUDAN® --, therefor.

In column 10, line 10, delete "INVITROGEN®." and insert -- INVITROGEN® --, therefor.

In column 10, line 30, delete "primer Pichia" and insert -- Primer pichia --, therefor.

In column 10, line 46, delete "zeocine" and insert -- zeocin --, therefor.

In column 16, line 50, in Claim 6, delete "factis," and insert -- lactis, --, therefor.

Signed and Sealed this

Seventeenth Day of August, 2010

David J. Kappos
*Director of the United States Patent and Trademark Office*